(12) United States Patent
Pasquet et al.

(10) Patent No.: US 10,561,598 B2
(45) Date of Patent: Feb. 18, 2020

(54) COMPOSITION COMPRISING A SILANE, A PARTICULAR FIXING POLYMER AND A CELLULOSE-BASED THICKENING POLYMER

(71) Applicant: L'OREAL, Paris (FR)

(72) Inventors: Dorothée Pasquet, Bois Colombes (FR); Cécile Bebot, Asnieres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/911,970

(22) PCT Filed: Aug. 7, 2014

(86) PCT No.: PCT/EP2014/066994
§ 371 (c)(1),
(2) Date: Feb. 12, 2016

(87) PCT Pub. No.: WO2015/022258
PCT Pub. Date: Feb. 19, 2015

(65) Prior Publication Data
US 2016/0193135 A1 Jul. 7, 2016

(30) Foreign Application Priority Data
Aug. 13, 2013 (FR) .................... 13 57967

(51) Int. Cl.
*A61K 8/81* (2006.01)
*A61K 8/58* (2006.01)
*A61K 8/73* (2006.01)
*A61Q 5/06* (2006.01)

(52) U.S. Cl.
CPC .............. *A61K 8/817* (2013.01); *A61K 8/585* (2013.01); *A61K 8/731* (2013.01); *A61K 8/8182* (2013.01); *A61Q 5/06* (2013.01); *A61K 2800/48* (2013.01)

(58) Field of Classification Search
CPC .... A61K 2800/48; A61K 8/585; A61K 8/731; A61K 8/817; A61K 8/8182
See application file for complete search history.

(56) References Cited

U.S. PATENT DOCUMENTS

| | | | |
|---|---|---|---|
| 3,910,862 A | 10/1975 | Barabas et al. | |
| 4,131,576 A | 12/1978 | Iovine et al. | |
| 4,165,367 A | 8/1979 | Chakrabarti | |
| 4,223,009 A | 9/1980 | Chakrabarti | |
| 2010/0254932 A1* | 10/2010 | Benabdillah | A61K 8/585 424/70.122 |
| 2012/0328550 A1* | 12/2012 | De Boni | A61K 8/361 424/70.6 |

FOREIGN PATENT DOCUMENTS

| | | |
|---|---|---|
| EP | 0080976 A1 | 6/1983 |
| EP | 2213334 A1 | 8/2010 |
| FR | 2077143 A5 | 10/1971 |
| FR | 2393573 A1 | 1/1979 |
| FR | 2910276 A1 | 6/2008 |
| FR | 2966356 A1 | 4/2012 |
| WO | 2006/018323 A1 | 2/2006 |

OTHER PUBLICATIONS

International Search Report for PCT/EP2014/066994, dated Sep. 29, 2014.
MINTEL: "Replenishing Radiance Masque," XP002724508, Jun. 2011.

* cited by examiner

*Primary Examiner* — Anna R Falkowitz
(74) *Attorney, Agent, or Firm* — The Marbury Law Group, PLLC

(57) ABSTRACT

The present invention relates to a composition comprising:
—(i) one or more cellulose-based thickening polymers;
—(ii) one or more cationic or nonionic fixing polymers other than (i); —(iii) one or more silanes corresponding to formula (I) below and/or oligomers thereof: $R_1Si(OR_2)_z(R_3)_x(OH)_y$ (I); the cellulose-based thickening polymer(s) being present in a concentration greater than or equal to 0.5% by weight relative to the total weight of the composition.

8 Claims, No Drawings

COMPOSITION COMPRISING A SILANE, A PARTICULAR FIXING POLYMER AND A CELLULOSE-BASED THICKENING POLYMER

CROSS REFERENCE TO RELATED APPLICATION

This is a national stage application of PCT/EP2014/066994, filed internationally on Aug. 7, 2014, which claims priority to French Application No. 1357967, which was filed on Aug. 13, 2013.

The present invention relates to a composition for treating keratin fibres, in particular human keratin fibres such as the hair, comprising one or more cellulose-based thickening polymers, one or more particular fixing polymers and one or more particular silanes.

The invention also relates to a cosmetic process for treating keratin fibres, especially a process for fixing and/or shaping keratin fibres using the abovementioned composition.

Finally, the invention relates to the use of the said composition for treating the hair, and in particular for styling the fibres, i.e. shaping and/or fixing the hairstyle.

In the field of styling, in particular among hair products intended for shaping and/or holding the hairstyle, the hair compositions that are the most widespread on the cosmetic market consist essentially of a solution, which is usually alcoholic or aqueous-alcoholic, and of one or more polymers, known as fixing polymers, which are generally film-forming polymers. These polymers thus have the function of making welds between the hairs so as to be able to fix the hairstyle in the desired shape. These fixing polymers are usually formulated as a mixture with various cosmetic adjuvants such as thickening polymers, which are generally anionic or nonionic.

Styling products may be in the form of gels, sera or foams that are generally applied to wet hair. To shape and fix the hairstyle, blow-drying or drying is then performed.

Moreover, styling products must especially be able to be spread onto the head of hair without leaving a tacky or dragging sensation during application.

However, styling products usually have the drawback of spreading poorly on the head of hair and of forming a dry, crumbly film, which, firstly, gives the hair a cosmetically unsatisfactory coarse feel, and, secondly, limits the hold of the hairstyle over time.

To improve the intensity and durability of the styling effects, it has already been proposed to use particular alkoxysilanes in styling compositions. Patent EP 2 213 334 in particular describes a composition comprising an alkoxysilane bearing a basic function combined with a microbial gum.

Patent FR 2 910 276 moreover describes a composition comprising an alkoxysilane comprising a solubilizing functional group combined with a cationic polymer. The fixing power of these compositions is occasionally insufficient in terms of intensity of fixing and durability, and the working properties are mediocre especially in terms of ease of application.

There is thus a real need to propose compositions for treating the hair, especially for styling the hair, which spread well onto the head of hair, which make it possible to obtain long-lasting fixing of the hairstyle and which give improved cosmetic properties while at the same time providing a good level of fixing so as to obtain satisfactory shaping and/or hold of the hairstyle.

The Applicant has discovered that by combining at least one cellulose-based thickening polymer, at least one cationic or nonionic fixing polymer and at least one particular silane, it is possible to obtain hair styling compositions with improved working qualities and improved styling performance.

One subject of the present invention is thus a composition comprising:
(i) one or more cellulose-based thickening polymers;
(ii) one or more cationic or nonionic fixing polymers other than (i);
(iii) one or more silanes corresponding to formula (I) below and/or oligomers thereof:

$$R_1Si(OR_2)_z(R_3)_x(OH)_y \qquad (I)$$

in which formula (I):
$R_1$ is a linear or branched, saturated or unsaturated, cyclic or acyclic $C_1$-$C_6$ hydrocarbon-based chain substituted with a group chosen from the following groups:
 amine $NH_2$ or NHR (R=$C_1$-$C_{20}$ and especially $C_1$-$C_6$ alkyl optionally substituted with a radical comprising a silicon atom, $C_3$-$C_{40}$ cycloalkyl or $C_6$-$C_{30}$ aromatic),
 or with a hydroxyl group,
 a thiol group,
 an aryl or aryloxy group which is unsubstituted or substituted, in particular with an amino group or with a $C_1$-$C_4$ aminoalkyl group;
$R_1$ possibly being interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2,
with z+x+y=3;
the cellulose-based thickening polymer(s) being present in a concentration greater than or equal to 0.5% by weight relative to the total weight of the composition.

Another subject of the invention consists of a composition that may be obtained by mixing two compositions, one comprising one or more compounds of formula (I) and/or oligomers thereof and the other comprising one or more cellulose-based thickening polymers and one or more cationic or nonionic fixing polymers.

This particular combination makes it possible to obtain compositions, especially in cream or gel form, which are easy to apply, which have an improved styling effect and an improved hair-densifying effect and which give the hair volume, while at the same time providing a good level of cosmetic fixing.

A subject of the invention is also a process for treating keratin fibres such as the hair, which consists in applying thereto the composition as defined previously.

A subject of the invention is also the use of the composition as defined previously, for treating keratin fibres and especially for holding and/or fixing the hair.

Silane

According to the invention, the composition comprises one or more silanes corresponding to formula (I) and/or oligomers thereof.

The term "oligomer" means the polymerization products of the compounds of formula (I) comprising from 2 to 10 silicon atoms.

Preferably, $R_2$ represents an alkyl group comprising from 1 to 4 carbon atoms, better still a linear alkyl group comprising from 1 to 4 carbon atoms, and preferably the ethyl group.

Preferably, $R_3$ represents an alkyl group comprising from 1 to 4 carbon atoms, better still a linear alkyl group comprising from 1 to 4 carbon atoms, and preferably methyl or ethyl groups.

Preferably, $R_1$ is an acyclic chain.

Preferably, the compound of formula (I) comprises only one silicon atom in its structure.

Preferably, $R_1$ represents an alkyl group, and even more preferentially a linear alkyl group, comprising from 1 to 6 carbon atoms or a $C_1$-$C_6$ aminoalkyl group.

Preferably, z ranges from 1 to 3. Even more preferentially, z is equal to 3.

Preferably, $R_1$ is a linear or branched, saturated or unsaturated C1-C6 hydrocarbon-based chain, substituted with an amine group NH2 or NHR (R=C1-C20 and especially C1-C6 alkyl, C3-C40 cycloalkyl or C6-C30 aromatic).

Preferably, the composition comprises at least one compound of formula (I) chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane, better still from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane or oligomers thereof, and, preferably, the silane is chosen from 3-aminopropyltriethoxysilane (APTES) or oligomers thereof, or mixtures thereof.

The silane(s) of formula (I) and/or oligomers thereof may be present in the composition according to the invention in a content ranging from 0.1% to 50% by weight, more preferentially from 0.5% to 20% by weight and better still from 1% to 15% by weight relative to the total weight of the composition.

Cellulose-Based Thickening Polymer

As indicated previously, the composition according to the invention comprises one or more cellulose-based thickening polymers.

For the purpose of the present invention, the term "thickening polymer" means a polymer which, when introduced at 1% in a pure aqueous solution or an aqueous-alcoholic solution containing 30% ethanol, and at pH=7, makes it possible to achieve a viscosity of at least 100 cps and preferably of at least 500 cps, at 25° C. and at a shear rate of 1 $s^{-1}$. This viscosity may be measured using a cone/plate viscometer (Haake R600 rheometer or the like).

Preferably, these polymers increase, through their presence, the viscosity of the compositions into which they are introduced by at least 50 cps and preferably at least 200 cps, at 25° C. and at a shear rate of 1 $s^{-1}$.

According to the invention, the term "cellulose-based" polymer means any polysaccharide compound having in its structure sequences of glucose residues bonded together via β-1,4 linkages.

The cellulose-based thickening polymer may be associative, i.e. it may bear in its structure at least one C10-$C_{30}$ fatty chain.

Alternatively, the cellulose-based thickening polymer may be non-associative, i.e. not bearing any C10-$C_{30}$ fatty chains.

The cellulose-based thickening polymers may be chosen from unsubstituted celluloses, especially in microcrystalline form, and cellulose derivatives which may be anionic, cationic, amphoteric or nonionic.

Among these cellulose-based polymers, cellulose ethers, cellulose esters and cellulose ester ethers are distinguished.

Among the cellulose esters are mineral esters of cellulose (cellulose nitrates, sulfates, phosphates, etc.), organic esters of cellulose (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers without a $C_{10}$-$C_{30}$ fatty chain, i.e. which are "non-associative", mention may be made of ($C_1$-$C_4$)alkylcelluloses, such as methylcelluloses and ethylcelluloses (for example, Ethocel standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$)alkyl($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hyd roxybutyl methylcellu loses.

Among the anionic cellulose ethers without a fatty chain, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers without a fatty chain, mention may be made of cationic cellulose derivatives such as cellulose copolymers or cellulose derivatives grafted with a water-soluble quaternary ammonium monomer, and described in particular in patent U.S. Pat. No. 4,131,576, such as (poly)hydroxy($C_1$-$C_4$)alkyl celluloses, for instance hydroxymethyl-, hydroxyethyl- or hydroxypropylcellu loses grafted especially with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

The associative cellulose-based thickening polymer may be cationic and may be chosen from:

quaternized cationic celluloses and in particular quaternized cationic hydroxyethylcelluloses modified with groups comprising at least one hydrophobic chain, preferably alkyl, alkylaryl or arylalkyl groups, or mixtures thereof, and preferably alkyl groups.

The alkyl radicals borne by the above quaternized celluloses or hydroxyethylcelluloses preferably comprise from 8 to 30 carbon atoms.

The aryl radicals preferably denote phenyl, benzyl, naphthyl or anthryl groups.

Examples of quaternized alkylhydroxyethylcelluloses containing C8-C30 hydrophobic chains that may be indicated include the products Quatrisoft LM 200®, Quatrisoft LM-X529-18-A®, Quatrisoft LM-X529-18B® (C12 alkyl) and Quatrisoft LM-X529-8® (C18 alkyl) sold by the company Amerchol and the products Crodacel QM®, Crodacel QL® (C12 alkyl) and Crodacel QS® (C18 alkyl) sold by the company Croda.

Mention may also be made of products such as Softcat Polymer SL 100 sold by the company Amerchol.

The associative cellulose-based thickening polymer may be nonionic and may be chosen from:

nonionic cellulose derivatives such as hydroxyethylcelluloses modified with groups comprising at least one hydrophobic chain, such as alkyl, arylalkyl or alkylaryl groups, or mixtures thereof, and in which the alkyl groups are preferably C8-C22, for instance the product Natrosol Plus Grade 330 CS® (C16 alkyls) sold by the company Aqualon, or the product Bermocoll EHM 100® sold by the company Berol Nobel, cellulose derivatives modified with alkylphenyl polyalkylene glycol ether groups, such as the product Amercell Polymer HM-1500® sold by the company Amerchol.

Among the cellulose-based thickening polymers that may be used in the composition according to the invention, cellulose ethers, and preferably nonionic cellulose ethers, are more particularly preferred.

Hydroxyalkylcelluloses, and in particular hydroxyethylcelluloses, will especially be used.

In a preferred variant of the invention, the cellulose-based thickening polymers are chosen from nonionic cellulose-based thickening polymers.

In another preferred variant of the invention, the cellulose-based thickening polymers are chosen from non-associative polymers, i.e. not bearing any $C_{10}$-$C_{30}$ fatty chains.

The cellulose-based thickening polymer(s) may be present in an amount ranging preferably from 0.5% to 10% by weight, better still from 0.5% to 5% by weight and even more preferentially from 0.5% to 2% by weight relative to the total weight of the composition.

Fixing Polymer

As indicated previously, the composition according to the invention comprises one or more nonionic fixing polymers or one or more cationic fixing polymers, or a mixture of these two types of polymer.

The term "fixing polymer" means any polymer that is capable of giving a shape to a head of hair or of retaining a head of hair in a given shape.

The nonionic fixing polymers that may be used according to the present invention are chosen, for example, from:

polyalkyloxazolines, vinyl acetate homopolymers, vinyl acetate copolymers, for instance copolymers of vinyl acetate and acrylic ester, copolymers of vinyl acetate and ethylene, or copolymers of vinyl acetate and maleic ester, for example dibutyl maleate, homopolymers and copolymers of acrylic esters, for instance copolymers of alkyl acrylates and alkyl methacrylates, such as the products provided by the company Röhm & Haas under the names Primal® AC-261 K and Eudragit® NE 30 D, by the company BASF under the name 8845, and by the company Hoechst under the name Appretan® N9212, copolymers of acrylonitrile and a nonionic monomer chosen, for example, from butadiene and alkyl (meth) acrylates, such as the products provided under the name CJ 0601 B by the company Röhm & Haas, styrene homopolymers, styrene copolymers, for instance copolymers of styrene and an alkyl (meth)acrylate, such as the products Mowilith® LDM 6911, Mowilith® DM 611 and Mowilith® LDM 6070 sold by the company Hoechst, the products Rhodopas® SD 215 and Rhodopas® DS 910 sold by the company Rhône-Poulenc, copolymers of styrene, alkyl methacrylate and alkyl acrylate, copolymers of styrene and butadiene, or copolymers of styrene, butadiene and vinylpyridine, polyamides, vinyllactam homopolymers such as vinylpyrrolidone homopolymers, such as the polyvinylcaprolactam sold under the name Luviskol® Plus by the company BASF, or the polyvinylpyrrolidone sold under the name PVP K30 L by the company ISP;

vinyllactam copolymers such as a poly(vinylpyrrolidone/ vinyllactam) copolymer sold under the trade name Luvitec® VPC 55K65W by the company BASF, poly (vinylpyrrolidone/vinyl acetate) copolymers, such as those sold under the name PVPVA® S630L by the company ISP, Luviskol® VA 73, VA 64, VA 55, VA 37 and VA 28 by the company BASF, and poly(vinylpyrrolidone/vinyl acetate/vinyl propionate) terpolymers, for instance the product sold under the name Luviskol® VAP 343 by the company BASF, and poly(vinyl alcohols).

The alkyl groups in the abovementioned nonionic polymers preferably contain from 1 to 6 carbon atoms.

Preferably, the nonionic fixing polymer(s) used according to the invention are chosen from vinyllactam homopolymers, such as vinylpyrrolidone homopolymers, polyvinylcaprolactam, and vinyllactam copolymers, such as a poly (vinylpyrrolidone/vinyllactam) copolymer, poly (vinylpyrrolidone/vinyl acetate) copolymers and poly (vinylpyrrolidone/vinyl acetate/vinyl propionate) terpolymers.

More preferentially, the nonionic fixing polymer(s) used according to the invention are chosen from vinyllactam homopolymers and copolymers, such as vinylpyrrolidone homopolymers and poly(vinylpyrrolidone/vinyl acetate) copolymers.

The cationic fixing polymers that may be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Among these polymers, mention may be made more particularly of the following cationic polymers:

(1) Homopolymers or copolymers derived from acrylic or methacrylic esters or amides and containing at least one of the units of formulae below:

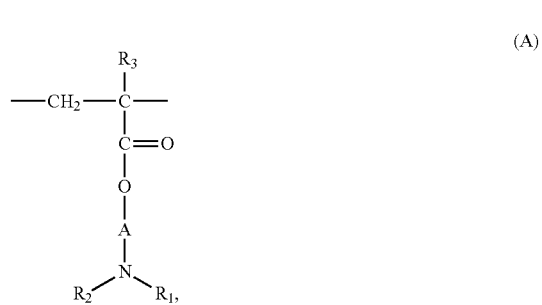

(A)

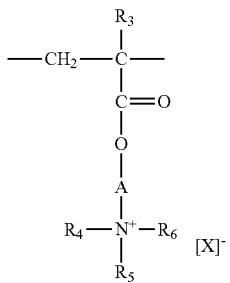

(B)

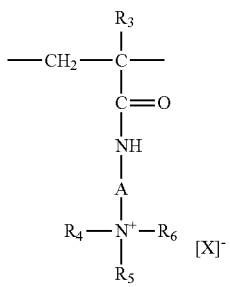

(C)

in which:

R₃ denotes a hydrogen atom or a CH₃ group;

A is a linear or branched alkyl group containing from 1 to 6 carbon atoms, or a hydroxyalkyl group containing from 1 to 4 carbon atoms;

R₄, R₅ and R₆, which may be identical or different, represent an alkyl group having from 1 to 18 carbon atoms, or a benzyl group;

R₁ and R₂, which may be identical or different, each represent a hydrogen atom or an alkyl group having from 1 to 6 carbon atoms;

X denotes a methosulfate anion or a halide such as chloride or bromide.

The copolymers of class (1) further contain one or more units deriving from comonomers which may be selected from the class of acrylamides, methacrylamides, diacetone acrylamides, acrylamides and methacrylamides substituted on the nitrogen by C₁-C₄ alkyl groups, groups derived from acrylic or methacrylic acids or esters thereof, vinyllactams such as vinylpyrrolidone or vinylcaprolactam, and vinyl esters.

Accordingly, these copolymers of class (1) may include the following:

copolymers of acrylamide and dimethylaminoethyl methacrylate quaternized with dimethyl sulfate or with a dimethyl halide, such as that sold under the name Hercofloc® by the company Hercules, copolymers of acrylamide and methacryloyloxyethyltrimethylammonium chloride, described for example in patent application EP-A-080976 and sold under the name Bina Quat P 100 by the company Ciba Geigy, the copolymer of acrylamide and methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573, polymers containing a fatty chain and a vinylpyrrolidone unit, such as the products sold under the names Styleze W20 and Styleze W10 by the company ISP, dimethylaminoethyl methacrylate/vinylcaprolactam/vinylpyrrolidone terpolymers, such as the product sold under the name Gaffix VC 713 or or under the name Advantage HC37 by the company ISP, and quaternized vinylpyrrolidone/dimethylaminopropylmethacrylamide copolymers, such as the products sold under the name Gafquat® HS 100 by the company ISP.

(2) Quaternary copolymers of vinylpyrrolidone and of vinylimidazole, such as the vinylimidazolium methosulfate/vinylcaprolactam/vinylpyrrolidone terpolymer sold under the name Luviquat Hold by the company BASF and the vinylpyrrolidone/methacrylamide/vinylimidazole/3-methyl-1-vinylimidazolium methyl sulfate (Polyquaternium 68) copolymer sold under the name Luviquat Supreme by the company BASF.

(3) Chitosans or salts thereof; the salts which can be used are more particularly the acetate, lactate, glutamate, gluconate or pyrrolidone carboxylate of chitosan.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(4) Polyvinylamine homopolymers and poly(vinylamine/N-vinylformamide) copolymers.

Among the cationic fixing polymers described above, it will be preferred to use:

a) those of class (1), preferably copolymers of acrylic or methacrylic esters bearing amino functions and especially those comprising at least one vinylpyrrolidone unit, for instance copolymers of vinylpyrrolidone and of dimethylaminoethyl methacrylate, such as the product sold under the name Copolymer 845 O by the company ISP and copolymers of vinylpyrrolidone, of dimethylaminoethyl methacrylate and of vinylcaprolactam, such as the product sold under the name Advantage HC 37 by the company ISP.

b) those of class (3), for instance quaternary copolymers of vinylpyrrolidone and of vinylimidazole, and more particularly the vinylimidazolium methosulfate/vinylcaprolactam/vinylpyrrolidone terpolymer sold under the name Luviquat Hold by the company BASF and the vinylpyrrolidone/methacrylamide/vinylimidazole/3-methyl-1-vinylimidazolium methyl sulfate (Polyquaternium 68) copolymer sold under the name Luviquat Supreme by the company BASF.

c) those of class (5) such as poly(vinylamine/N-vinylformamide) such as the product sold under the name Luviquat 9030 by the company BASF.

In a preferred variant of the invention, the fixing polymers are chosen from nonionic polymers.

The nonionic or cationic fixing polymer(s) are preferably present in the composition in an amount of from 0.1% to 20% by weight, better still from 0.2% to 10% by weight and even more preferentially from 0.5% to 5% by weight relative to the total weight of the composition.

The composition according to the invention preferably comprises water. Preferably, the water content ranges from 10% to 98%, preferably from 20% to 96%, better still from 50% to 96% by weight and even better still from 70% to 96% by weight relative to the total weight of the composition.

The composition may also comprise one or more organic solvents, such as C₁-C₄ lower alcohols, such as ethanol, isopropanol, tert-butanol or n-butanol; polyols such as propylene glycol; polyol ethers; $C_5$-$C_{10}$ alkanes; $C_3$-$C_4$ ketones, such as acetone and methyl ethyl ketone; $C_1$-$C_4$ alkyl acetates, such as methyl acetate, ethyl acetate and butyl acetate; dimethoxyethane, diethoxyethane; and mixtures thereof.

The composition of the invention may also comprise at least one common cosmetic ingredient, chosen especially from anionic, cationic and nonionic surfactants, oils; solid fatty substances and especially $C_8$-$C_{40}$ esters, $C_8$-$C_{40}$ acids; $C_8$-$C_{40}$ alcohols, sunscreens; moisturizers; antidandruff agents; antioxidants; chelating agents; nacreous agents and opacifiers; plasticizers or coalescers; fillers, especially mineral fillers; glitter flakes; silicones, especially silicone gums, alkoxylated or non-alkoxylated silicones; polymeric or non-polymeric thickeners or gelling agents, other than the cellulose-based thickening polymers; emulsifiers; polymers, other than those mentioned previously, especially conditioning polymers; fragrances; preserving agents; basifying agents, such as sodium hydroxide, or acidifying agents; silanes other than those described previously; crosslinking agents; dyes. The composition can, of course, comprise several cosmetic ingredients appearing in the above list.

Depending on their nature and the purpose of the composition, the normal cosmetic ingredients can be present in normal amounts which can be easily determined by those skilled in the art and which can be, for each ingredient, between 0.01% and 80% by weight. A person skilled in the art will take care to choose the ingredients included in the composition, and also the amounts thereof, such that they do not harm the properties of the compositions of the present invention.

The compositions in accordance with the invention can be packaged for example in a jar, in a tube, in a pump-dispenser bottle, in a foamer or in an aerosol device that is customary in the cosmetics industry.

The compositions according to the invention can, when they are intended to be packaged in an aerosol device, contain one or more propellant gases.

The propellant gas can then be chosen, for example, from volatile hydrocarbons, such as, in particular, $C_1$ to $C_4$ alkanes and preferably n-butane, propane, isobutane and mixtures thereof, chlorinated and/or fluorinated hydrocarbons, dimethyl ether and mixtures of these gases.

When it contains same, the composition comprises a propellant gas in a content ranging from 1% to 50% by weight and more preferentially from 1% to 10% by weight, relative to the total weight of said composition.

The compositions according to the invention can be, inter alia, in the form of liquids which are thickened to a lesser or greater extent, of gels, of creams, of pastes or of foams.

Preferably, they are in the form of gels or creams.

In a preferred variant, the viscosity of the compositions of the invention is greater than or equal to 2 poises, better still greater than or equal to 5 poises and even better still greater than or equal to 7 poises at 25° C. and at a shear rate of 1 $s^{-1}$. This viscosity may be determined with a rheometer with cone-plate geometry.

The composition according to the invention may be advantageously used for hair treatment. In particular, it may be used for hairstyling, for example for shaping and/or fixing the hairstyle.

According to one particularly preferred embodiment, it is used for simultaneously styling and conditioning the hair.

The present invention also relates to a process, especially a cosmetic process, for treating the hair, for example a process for shaping and/or holding the hairstyle, which consists in applying to the hair an effective amount of a composition as described above.

Preferably, the composition according to the invention is not rinsed off.

The examples that follow serve to illustrate the invention without, however, being limiting in nature.

EXAMPLES

In the following examples, all the amounts are given as mass percentages of active material relative to the total weight of the composition.

The compositions according to the invention are prepared from the compounds indicated in the table below.

| INCI Name | Trade Names | A | B | C | D |
| --- | --- | --- | --- | --- | --- |
| Aminopropyltriethoxysilane | KBE-903 (Shin-Etsu) | 2 | 3.7 | 10 | 1 |
| Polyquaternium-4 | Celquat LOR (Akzo Nobel) | — | — | — | — |
| Polyquaternium-68 | Luviquat Supreme (BASF) (20% AM) | 0.3 | — | — | — |
| Polyquaternium-46 | Luviquat Hold AT 2 (BASF) (20% AM) | — | — | 10.2 | — |
| Vinylamine/vinylformamide copolymer | Luviquat 9030 (BASF) (13% AM) | — | — | 0.13 | |
| VP/dimethylaminoethyl methacrylate copolymer | Copolymer 845-O (ISP) (19.85% AM) | — | — | — | 0.49 |
| Vinylcaprolactam/VP/dimethyl aminoethyl methacrylate copolymer | Advantage HC 37 (ISP) (18.85% AM) | — | — | — | 0.13 |
| VP/VA copolymer | Luviskol VA 64 W (BASF) (50% AM) | — | 2 | — | — |
| PVP | PVP K 30L (ISP) | | | 0.5 | |
| Hydroxyethylcellulose | Natrosol 250 HHR PC (Ashland) | 1.7 | 1.5 | 2 | 0.8 |
| Amodimethicone (and) trideceth-6 (and) cetrimonium chloride | Xiameter MEM-8299 emulsion (Dow Corning) (63.42% AM) | — | 0.5 | — | — |
| PEG-40 hydrogenated castor oil | Eumulgin HRE 40 (BASF) | 0.7 | 0.5 | 0.7 | 0.8 |
| Propylene glycol | Propylene glycol USP/EP (Dow Chemical) | — | 3 | — | — |

-continued

| INCI Name | Trade Names | A | B | C | D |
|---|---|---|---|---|---|
| Fragrance | | 0.2 | 0.3 | 0.2 | 0.2 |
| Preserving agents | | 0.9 | 0.9 | 0.7 | 0.7 |
| Hydrochloric acid | SQ hydrochloric acid (Qualigens Fine Chemicals) (33.5%) | 0.23 | — | — | — |
| Lactic acid | Purac HS88 (Purac) (90%) | — | 0.72 | 2.25 | 0.27 |
| Water | | qs 100 | qs 100 | qs 100 | qs 100 |

These compositions are in the form of creams or gels.

The compositions of Examples A to D according to the invention were applied to wet or dry hair without final rinsing. The application is performed easily.

It is observed that after drying, a good styling effect is obtained (good level of fixing and long-lasting) with a provision of volume and a good feel.

The invention claimed is:

1. A composition comprising:
   (i) at least one thickening polymer chosen from hydroxyethylcelluloses;
   (ii) at least one fixing polymer chosen from vinyl acetate copolymers; and
   (iii) at least one silane chosen from 3-aminopropyltriethoxysilane, oligomers thereof, and mixtures thereof,
   wherein the at least one thickening polymer is present in the composition in a concentration ranging from 0.5% to 2% by weight, relative to the total weight of the composition.

2. The composition of claim 1, wherein the at least one fixing polymer comprises poly(vinylpyrrolidone/vinyl acetate).

3. The composition of claim 1, wherein the at least one silane is present in the composition in concentration ranging from about 0.1% to about 50% by weight, relative to the total weight of the composition.

4. The composition of claim 1, wherein the at least one thickening polymer is present in the composition in a concentration ranging from about 0.8% to about 2.0% by weight, relative to the total weight of the composition.

5. The composition of claim 1, wherein the at least one fixing polymer is present in the composition in a concentration ranging from about 0.1% to about 20% by weight, relative to the total weight of the composition.

6. The composition of claim 1, wherein the composition is aqueous.

7. The composition of claim 1, wherein the composition is obtained by mixing:
   a first composition comprising the least one silane, and
   a second composition comprising the at least one thickening polymer and the at least one fixing polymer.

8. A process for treating keratin fibers, comprising applying to the keratin fibers a composition, said composition comprising:
   (i) at least one thickening polymer chosen from hydroxyethylcelluloses;
   (ii) at least one fixing polymer chosen from vinyl acetate copolymers; and
   (iii) at least one silane chosen from 3-aminopropyltriethoxysilane, oligomers thereof, and mixtures thereof,
   wherein the at least one thickening polymer is present in the composition in a concentration ranging from 0.5% to 2% by weight, relative to the total weight of the composition.

* * * * *